US 11,286,224 B2

(12) United States Patent
Hickmann et al.

(10) Patent No.: US 11,286,224 B2
(45) Date of Patent: Mar. 29, 2022

(54) SYNTHESIS OF ALIPHATIC ALCOHOLS AS AROMA CHEMICALS

(71) Applicant: BASF SE, Ludwigshafen am Rhein (DE)

(72) Inventors: Volker Hickmann, Ludwigshafen am Rhein (DE); Shrirang Hindalekar, Mumbai (IN); Nitin Gupte, Mumbai (IN); Sadanand Ardekar, Mumbai (IN); Wolfgang Siegel, Ludwigshafen am Rhein (DE); Vijay Narayanan Swaminathan, Ludwigshafen am Rhein (DE); Ralf Pelzer, Lampertheim (DE)

(73) Assignee: BASF SE, Ludwigshafen am Rhein (DE)

( * ) Notice: Subject to any disclaimer, the term of this patent is extended or adjusted under 35 U.S.C. 154(b) by 48 days.

(21) Appl. No.: 16/755,308

(22) PCT Filed: Oct. 4, 2018

(86) PCT No.: PCT/EP2018/076953
§ 371 (c)(1),
(2) Date: Apr. 10, 2020

(87) PCT Pub. No.: WO2019/072669
PCT Pub. Date: Apr. 18, 2019

(65) Prior Publication Data
US 2021/0188748 A1 Jun. 24, 2021

(30) Foreign Application Priority Data
Oct. 13, 2017 (EP) .................................... 17196267

(51) Int. Cl.
*C07C 29/44* (2006.01)
*C11B 9/00* (2006.01)
*C07C 29/60* (2006.01)
*C07C 33/025* (2006.01)

(52) U.S. Cl.
CPC .............. *C07C 29/44* (2013.01); *C07C 29/60* (2013.01); *C07C 33/025* (2013.01); *C11B 9/0015* (2013.01); *C07B 2200/09* (2013.01)

(58) Field of Classification Search
CPC ........ C07C 29/44; C07C 29/60; C11B 9/0015
See application file for complete search history.

(56) References Cited

U.S. PATENT DOCUMENTS

| 3,959,396 A | 5/1976 | Ochsner et al. |
| 4,006,109 A | 2/1977 | Ochsner et al. |
| 6,297,211 B1 | 10/2001 | Frater et al. |

FOREIGN PATENT DOCUMENTS

| CH | 549635 A | 5/1974 |
| EP | 1029841 B1 | 4/2003 |
| GB | 1301596 A | 12/1972 |
| GB | 1311600 A | 3/1973 |

OTHER PUBLICATIONS

Brunel et al., "Reaction of non Stabilised Phosphonium Ylides with Lactones", Tetrahedron Letters, Elsevier, Amsterdam, NL, vol. 37, No. 22, May 1, 1996, pp. 3853-3856.
European Search Report for EP Application No. 17196267.3, dated Jan. 19, 2018, 3 pages.
International Preliminary Report on Patentability received for PCT Patent Application No. PCT/EP2018/076953, dated Apr. 14, 2020, 7 pages.
International Search Report for PCT/EP2018/076953 dated Dec. 4, 2018.
Written Opinion of the International Searching Authority for PCT/EP2018/076953 dated Dec. 4, 2018.

*Primary Examiner* — Sikarl A Witherspoon
(74) *Attorney, Agent, or Firm* — Faegre Drinker Biddle & Reath LLP

(57) ABSTRACT

The present invention relates to a method for preparing a compound of formula (I). The present invention also relates to compounds of formula (A) or a compound in the form of a stereoisomer. The present invention further relates to the use of a compound of formula (A) as aroma chemical.

formula (I)

19 Claims, No Drawings

SYNTHESIS OF ALIPHATIC ALCOHOLS AS AROMA CHEMICALS

CROSS-REFERENCE TO RELATED APPLICATIONS

This application is a national stage application (under 35 U.S.C. § 371) of PCT/EP2018/076953, filed Oct. 4, 2018, which claims benefit of European Application No. 17196267.3, filed Oct. 13, 2017, both of which are incorporated herein by reference in their entirety.

FIELD OF THE INVENTION

The present invention relates to a method for preparing a compound of formula (I). The present invention also relates to compounds of formula (A) or a compound in the form of a stereoisomer. The present invention further relates to the use of compound of formula (A) as aroma chemical.

BACKGROUND OF THE INVENTION

DE 1,311,600 describes a process for the preparation of a mixture of racemic 6-ethyl-2-methyl-octen-(5)-ol-(1) and 6-ethyl-2-methyl-octen-(6)-of-(1) starting from diethyl ketone. Here, the diethyl ketone is condensed with a mixture of cis- and trans-penten-(2)-yn-(4)-ol-(1) in the presence of potassium hydroxide to get a mixture of cis- and trans-6-ethyl-octen-(2)-yne-(4)-diol-(1,6) which is hydrogenated in the presence of hydrogen and Raney-Ni to get 6-ethyl-octanediol-(1,6). The saturated diol is dehydrated in the presence of potassium bisulfate at a temperature of 150°-160° C. to result in a crude mixture of cis- and trans-6-ethyl-octen-(5)-ol-(1) and 6-ethyl-octen-(6)-ol-(1) after repeated washings with sodium carbonate solution and water. The mixture of cis- and trans-6-ethyl-octen-(5)-ol-(1) and 6-ethyl-octen-(6)-ol-(1) is further reacted with sodium methylate in the presence of zinc oxide to give a mixture of 6-ethyl-2-methyl-octen-(5)-ol-(1) and 6-ethyl-2-methyl-octen-(6)-of-(1). This synthesis would not appear to be very suitable for an industrial process on account of tedious work-up procedures and low yields.

The preparation of (6E)-3,6-dimethyloct-6-en-1-ol and (6Z)-3,6-dimethyloct-6-en-1-ol is achieved by EP 1,029,841 B1 by reaction of the Grignard reagent of THP-protected 5-bromo-3-methylpentan-1-ol with acetaldehyde, subsequent Dess-Martin oxidation, followed by Wittig reaction with ethyl triphenyl phosphonium bromide and acid-catalysed deprotection.

The present invention relates to a process for the preparation of aliphatic alcohols as aroma chemicals. It is an object of the present invention to decrease or minimize the number of reaction steps for preparation of aliphatic alcohols without impairing the yield. It is also an object of the present invention to provide a flexibility of preparing various substituted aliphatic alcohols without further increase in the number of steps. The present invention also relates to compounds of formula (A) or a compound in the form of a stereoisomer. The present invention further relates to the use of compound of formula (A) as aroma chemical.

SUMMARY OF THE INVENTION

The inventors have surprisingly found that this object is achieved, and the present invention process has the following advantages:

The process is viable on industrial scale.

The modification of substituents on the aliphatic alcohol chain is carried out without increasing the number of steps or impairing the yield.

Since protecting groups usually increase the number of steps of a synthesis and increase the amount of waste generated, the present invention process sequence does not use any protecting groups.

Hence, the invention provides a method for preparing a compound of formula (I)

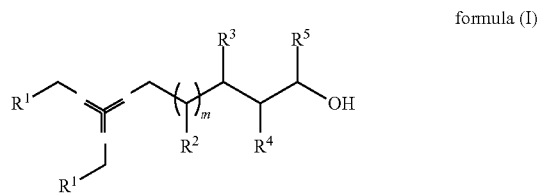

formula (I)

wherein $=\!=\!=$ is a single or a double bond, wherein formula (I) comprises the compound of the formula (Ia)

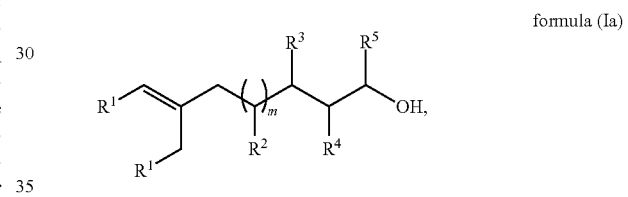

formula (Ia)

the compound of the formula (Ib)

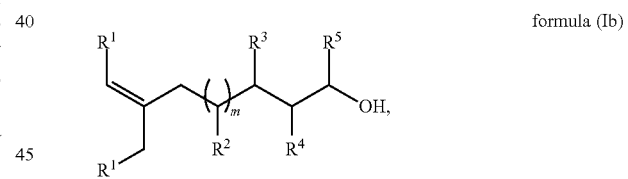

formula (Ib)

and the compound of the formula (Ic)

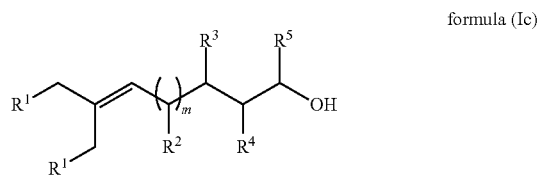

formula (Ic)

and stereoisomers thereof;

whereby m is 0; $R^1$, $R^3$, $R^4$ and $R^5$, identical or different, are selected from the group consisting of H, $C_1$-$C_4$-alkyl and $C_3$-$C_4$-cycloalkyl;

whereby m is 1, 2 or 3; $R^1$, $R^2$, $R^3$, $R^4$ and $R^5$, identical or different, are selected from the group consisting of H, $C_1$-$C_4$-alkyl and $C_3$-$C_4$-cycloalkyl;

comprising at least the steps of:
a) providing a compound of formula (IIa),

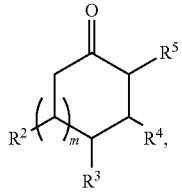

formula (IIa)

whereby m is 0; $R^3$, $R^4$ and $R^5$, identical or different, are selected from the group consisting of H, $C_1$-$C_4$-alkyl and $C_3$-$C_4$-cycloalkyl; whereby m is 1, 2 or 3 and $R^2$, $R^3$, $R^4$ and $R^5$, identical or different, are selected from the group consisting of H, $C_1$-$C_4$-alkyl and $C_3$-$C_4$-cycloalkyl;

b) subjecting the compound of the formula (IIa) to a compound selected from peroxyacids and peroxides to obtain a compound of formula (IIb),

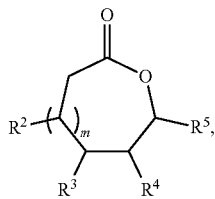

formula (IIb)

c) reacting the compound of the formula (IIb) with a compound of formula (IIc), $R^1CH_2MgX$     formula (IIc), wherein $R^1$ is selected from the group consisting of H, $C_1$-$C_4$-alkyl and $C_3$-$C_4$-cycloalkyl; X is Cl, Br or I, to obtain a compound of formula (IId),

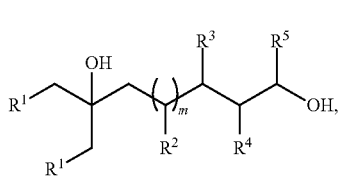

formula (IId)

whereby m is 0; $R^1$, $R^3$, $R^4$ and $R^5$, identical or different, are selected from the group consisting of H, $C_1$-$C_4$-alkyl and $C_3$-$C_4$-cycloalkyl;

whereby m is 1, 2 or 3 and $R^1$, $R^2$, $R^3$, $R^4$ and $R^5$, identical or different, are selected from the group consisting of H, $C_1$-$C_4$-alkyl and $C_3$-$C_4$-cycloalkyl;

d) subjecting the compound of formula (IId) to a dehydration reaction to obtain the compound of the formula (I).

In a preferred embodiment, the invention provides a method for preparing a compound of formula (I')

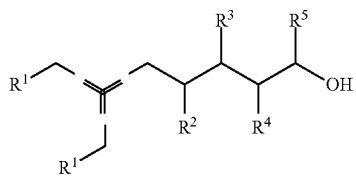

formula (I')

wherein

═══ is a single or a double bond,
wherein formula (I') comprises
the compound of the formula (Ia')

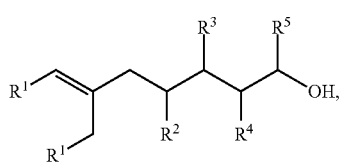

formula (Ia')

the compound of the formula (Ib')

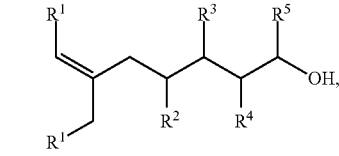

formula (Ib')

the compound of the formula (Ic')

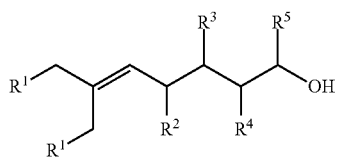

formula (Ic')

and
stereoisomers thereof;
wherein $R^1$, $R^2$, $R^3$, $R^4$ and $R^5$, identical or different, are selected from the group consisting of H, $C_1$-$C_4$-alkyl and $C_3$-$C_4$-cycloalkyl;
comprising at least the steps of:
a) providing a compound of formula (IIa')

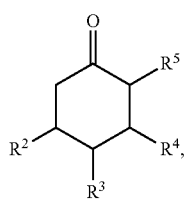

formula (IIa')

wherein $R^2$, $R^3$, $R^4$ and $R^5$, identical or different, are selected from the group consisting of H, $C_1$-$C_4$-alkyl and $C_3$-$C_4$-cycloalkyl;

b) subjecting the compound of the formula (IIa) to a compound selected from peroxyacids and peroxides to obtain a compound of formula (IIb'),

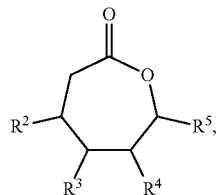

formula (IIb')

c) reacting the compound of the formula (IIb') with a compound of formula (IIc'), $R^1CH_2MgX$   formula (IIc')

wherein $R^1$ is selected from the group consisting of H, $C_1$-$C_4$-alkyl and $C_3$-$C_4$-cycloalkyl; X is Br, Cl or I, to obtain a compound of formula (IId'),

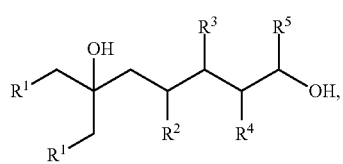

formula (IId')

wherein $R^1$, $R^2$, $R^3$, $R^4$ and $R^5$, identical or different, are selected from the group consisting of H, $C_1$-$C_4$-alkyl and $C_3$-$C_4$-cycloalkyl;

d) subjecting the compound of formula (IId') to a dehydration reaction to obtain the compound of the formula (I').

The invention further provides a compound of the formula A

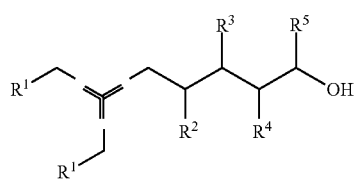

formula A wherein
 is a single or a double bond,
wherein formula A comprises
the compound of the formula (A.a),

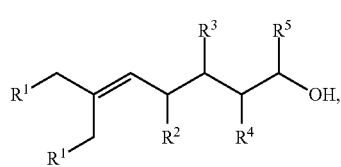

formula (A.a)

the compound of the formula (A.b),

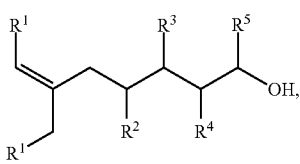

formula (A.b)

and
the compound of the formula (A.c)

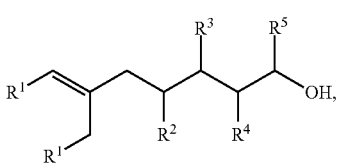

formula (A.c)

wherein $R^1$, $R^2$ and $R^5$, identical or different, are selected from the group consisting of H, $C_1$-$C_4$-alkyl and $C_3$-$C_4$-cycloalkyl;
$R^4$ is selected from the group consisting of H, $C_2$-$C_4$-alkyl and $C_3$-$C_4$-cycloalkyl;
$R^3$ is H;
and stereoisomers thereof, with a proviso that at least one of the $R^1$, $R^2$, $R^4$ and $R^5$ is not H.

The invention further relates to a composition comprising at least one compound selected from the compound of the formula A, preferably the mixture of compounds of the formulae (A.a), (A.b) and (A.c). The invention also relates to the use of a compound of the formula A as aroma chemical.

DESCRIPTION OF THE INVENTION

In one embodiment, the invention provides a method for preparing a compound of formula (I)

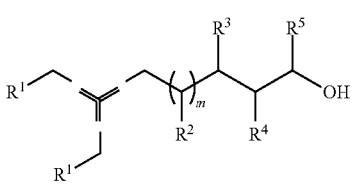

formula (I)

wherein
 is a single or a double bond,
wherein formula (I) comprises
the compound of the formula (Ia)

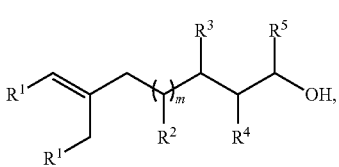

formula (Ia)

the compound of the formula (Ib)

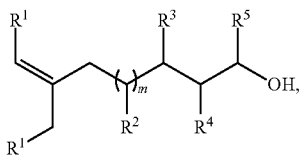
formula (Ib)

and
the compound of the formula (Ic)

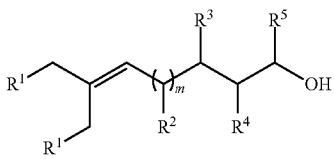
formula (Ic)

and stereoisomers thereof;
whereby m is 0; $R^1$, $R^3$, $R^4$ and $R^5$, identical or different, are selected from the group consisting of H, $C_1$-$C_4$-alkyl and $C_3$-$C_4$-cycloalkyl;
whereby m is 1, 2 or 3; $R^1$, $R^2$, $R^3$, $R^4$ and $R^5$, identical or different, are selected from the group consisting of H, $C_1$-$C_4$-alkyl and $C_3$-$C_4$-cycloalkyl;
comprising at least the steps of:
a) providing a compound of formula (IIa),

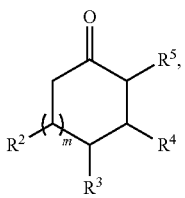
formula (IIa)

whereby m is 0; $R^3$, $R^4$ and $R^5$, identical or different, are selected from the group consisting of H, $C_1$-$C_4$-alkyl and $C_3$-$C_4$-cycloalkyl;
whereby m is 1, 2 or 3 and $R^2$, $R^3$, $R^4$ and $R^5$, identical or different, are selected from the group consisting of H, $C_1$-$C_4$-alkyl and $C_3$-$C_4$-cycloalkyl;
b) subjecting the compound of the formula (IIa) to a compound selected from peroxyacids and peroxides to obtain a compound of formula (IIb),

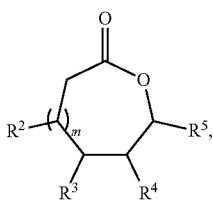
formula (IIb)

c) reacting the compound of the formula (IIb) with a compound of formula (IIc), $R^1CH_2MgX$   formula (IIc), wherein $R^1$ is selected from the group consisting of H, $C_1$-$C_4$-alkyl and $C_3$-$C_4$-cycloalkyl, to obtain a compound of formula (IId),

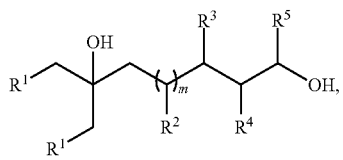
formula (IId)

whereby m is 0; $R^1$, $R^3$, $R^4$ and $R^5$, identical or different, are selected from the group consisting of H, $C_1$-$C_4$-alkyl and $C_3$-$C_4$-cycloalkyl;
whereby m is 1, 2 or 3 and $R^1$, $R^2$, $R^3$, $R^4$ and $R^5$, identical or different, are selected from the group consisting of H, $C_1$-$C_4$-alkyl and $C_3$-$C_4$-cycloalkyl;
d) subjecting the compound of formula (IId) to a dehydration reaction to obtain the compound of the formula (I).

Although the present invention will be described with respect to particular embodiments, this description is not to be construed in a limiting sense.

Before describing in detail exemplary embodiments of the present invention, definitions important for understanding the present invention are given. As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the present invention the term "consisting of" is considered to be a preferred embodiment of the term "comprising of".

In a preferred embodiment, the invention provides a method for preparing a compound of formula (I')

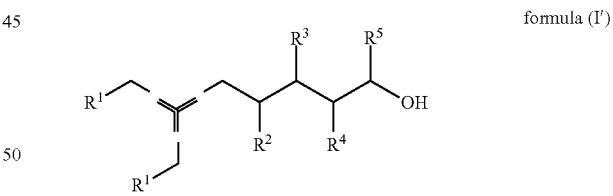
formula (I')

wherein
⸺ is a single or a double bond,
wherein formula (I') comprises
the compound of the formula (Ia')

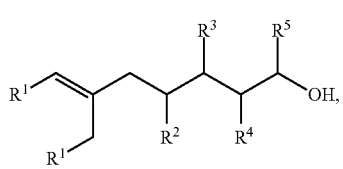
formula (Ia')

the compound of the formula (Ib')

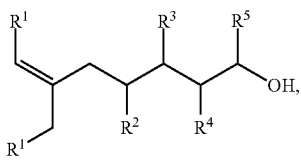

formula (Ib')

and
the compound of the formula (Ic')

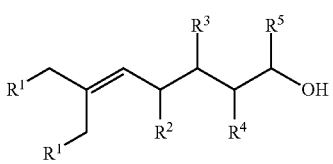

formula (Ic')

and stereoisomers thereof;
wherein $R^1$, $R^2$, $R^3$, $R^4$ and $R^5$, identical or different, are selected from the group consisting of H, $C_1$-$C_4$-alkyl and $C_3$-$C_4$-cycloalkyl;
comprising at least the steps of:
a) providing a compound of formula (IIa'),

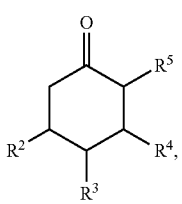

formula (IIa')

wherein $R^2$, $R^3$, $R^4$ and $R^5$, identical or different, are selected from the group consisting of H, $C_1$-$C_4$-alkyl and $C_3$-$C_4$-cycloalkyl;
b) subjecting the compound of the formula (IIa) to a compound selected from peroxyacids and peroxides to obtain a compound of formula (IIb'),

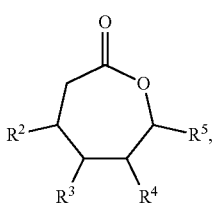

formula (IIb')

c) reacting the compound of the formula (IIb') with a compound of formula (IIc'),

formula (IIc'), wherein $R^1$ is selected from the group consisting of H, $C_1$-$C_4$-alkyl and $C_3$-$C_4$-cycloalkyl; X is Br, Cl or I, to obtain a compound of formula (IId'),

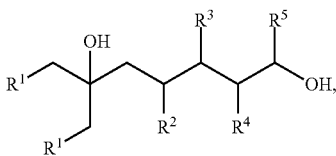

formula (IId')

wherein $R^1$, $R^2$, $R^3$, $R^4$ and $R^5$, identical or different, are selected from the group consisting of H, $C_1$-$C_4$-alkyl and $C_3$-$C_4$-cycloalkyl;
d) subjecting the compound of formula (IId') to a dehydration reaction to obtain the compound of the formula (I').

In another embodiment, the process steps (b), (c) and (d) and/or steps (b) and (c) and/or steps (c) and (d) are carried out in a single pot.

In yet another embodiment, the peroxyacid in step b) is selected from the group consisting of peroxymonosulfuric acid, peroxyphosphoric acid, peroxyacetic acid, peroxyformic acid, peroxytrifluoroacetic acid, potassium peroxymonosulfate, sodium perborate, peroxynitric acid and peroxybenzoic acid. In a preferred embodiment, the peroxybenzoic acid is metachloroperoxybenzoic acid.

In yet another preferred embodiment, the peroxide in step b) is hydrogen peroxide. In a preferred embodiment, the temperature in step b) is in the range of $\geq 0°$ C. to $\leq 70°$ C., in particular, the temperature is in the range of $\geq 20°$ C. to $\leq 60°$ C.

In another embodiment, in step b) the molar ratio of the compound selected from peroxyacids and peroxides to the compound of formula (IIa) is in the range of $\geq 1$ to $\leq 3.0$, in particular, in the range of $\geq 1.1$ to $\leq 2.0$.

In another preferred embodiment, in step c) the temperature is in the range of $\geq -20°$ C. to $\leq 50°$ C., preferably, the temperature is in the range of $\geq 0°$ C. to $\leq 20°$ C.

In yet another embodiment, in step c) the molar ratio of the compound of formula (IIc) to the compound of formula (IIb) is in the range of $\geq 2$ to $\leq 5.0$, in particular, in the range of $\geq 2.5$ to $\geq 5.0$.

In an embodiment, the step d) is carried out in the presence of an acid, particularly, the acid is selected from the group consisting of methanesulfonic acid, phosphoric acid, p-toluenesulfonic acid, formic acid, sulfuric acid, hydrochloric acid and acetic acid, preferably, p-toluenesulfonic acid, more preferably, methanesulfonic acid.

In another embodiment, in step d) the temperature is in the range of $\leq 0°$ C. to $\geq 80°$ C., preferably, in the range of $\leq 10°$ C. to $\geq 40°$ C.

In yet another embodiment, in step d) the molar ratio of the acid to the compound of formula (IIc) is in the range of $\leq 0.2$ to $\geq 4.0$, in particular, in the range of $\leq 0.2$ to $\geq 2.5$.

In one embodiment, the present invention provides a compound of the formula A

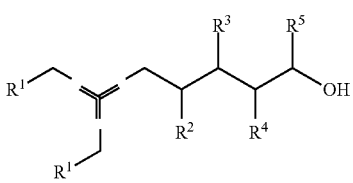

formula A wherein
⸺ is a single or a double bond,
wherein formula A comprises
the compound of the formula (A.a),

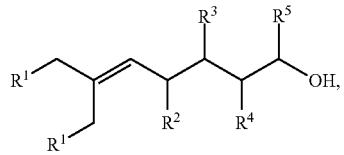

formula (A.a)

the compound of the formula (A.b),

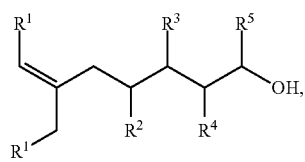

formula (A.b)

and
the compound of the formula (A.c)

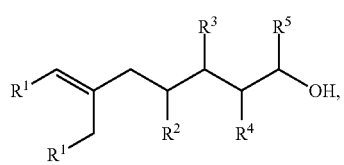

formula (A.c)

wherein $R^1$, $R^2$ and $R^5$, identical or different, are selected from the group consisting of H, $C_1$-$C_4$-alkyl and $C_3$-$C_4$-cycloalkyl;
$R^4$ is selected from the group consisting of H, $C_2$-$C_4$-alkyl and $C_3$-$C_4$-cycloalkyl;
$R^3$ is H;
and stereoisomers thereof, with a proviso that at least one of the $R^1$, $R^2$, $R^4$ and $R^5$ is not H.

In preferred embodiment, $R^1$ is H or methyl and $R^3$ is H.

In yet another preferred embodiment, $R^2$ and $R^5$, identical or different, are selected from the group consisting of H, methyl, ethyl, 1-propyl, 1-methylethyl, and cyclopropyl. In particular, $R^2$ is H or methyl. More preferably, $R^5$ is methyl or 1-methylethyl.

In one embodiment, the present invention provides a compound of the formula A

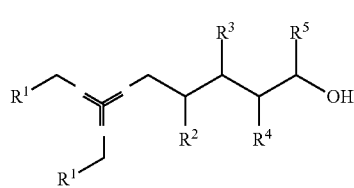

formula A wherein
⸺ is a single or a double bond,
wherein formula A comprises
the compound of the formula (A.a),

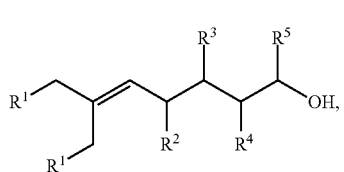

formula (A.a)

the compound of the formula (A.b),

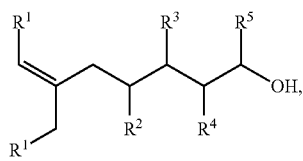

formula (A.b)

and
the compound of the formula (A.c)

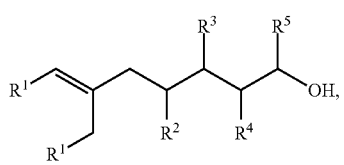

formula (A.c)

wherein $R^1$, $R^2$ and $R^5$, identical or different, are selected from the group consisting of H, $C_1$-$C_4$-alkyl and $C_3$-$C_4$-cycloalkyl;
$R^4$ is selected from the group consisting of H, $C_2$-$C_4$-alkyl and $C_3$-$C_4$-cycloalkyl; $R^3$ is H;
and stereoisomers thereof, with a proviso that when $R^1$ is H or methyl then at least one of the $R^2$, $R^4$ and $R^5$ is not H.

In preferred embodiment, the present invention provides the compound of formula A, wherein $R^1$ is H or methyl; $R^2$ is selected from the group consisting of H, methyl, ethyl, 1-propyl, 1-methylethyl, and cyclopropyl; $R^5$ is selected from the group consisting of methyl, ethyl, 1-propyl, 1-methylethyl, and cyclopropyl; $R^4$ is selected from the group consisting of H, ethyl, 1-propyl, 1-methylethyl, and cyclopropyl; and $R^3$ is H.

In yet another preferred embodiment, $R^4$ is selected from the group consisting of H, ethyl, 1-propyl, 1-methylethyl, and cyclopropyl;

In preferred embodiment, the compound of formula A is selected from the compounds of formulae (A.a2), (A.b2), (A.c2), (A.a3), (A.b3) and (A.c3).

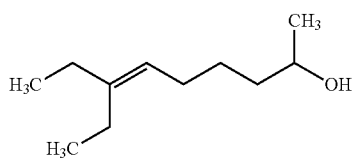

(A.a2)

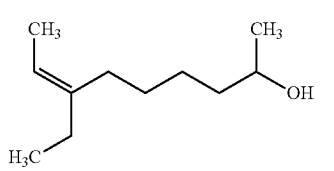
(A.b2)

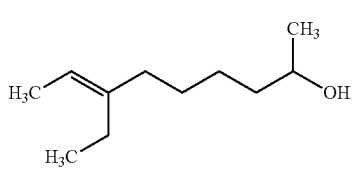
(A.c2)

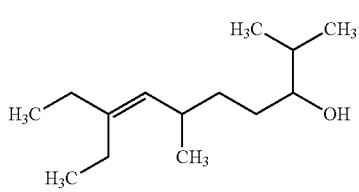
(A.a3)

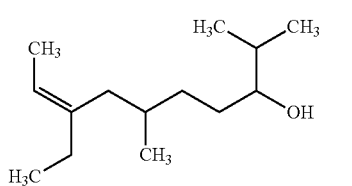
(A.b3)

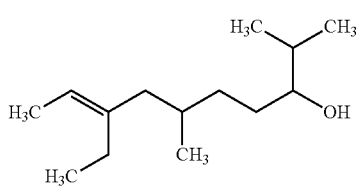
(A.c3)

and stereoisomers thereof.

In one embodiment, the present invention relates to a composition comprising at least one compound selected from the compound of the formula A, preferably the mixture of compounds of the formulae (A.a), (A.b) and (A.c).

In a preferred embodiment, the compositions according to the invention comprise at least two compounds selected from the compounds of the formulae A, preferably the mixture of compounds of the formulae (A.a), (A.b) and (A.c).

In another embodiment, the present invention relates to the use of a compound of the formula A or of a composition comprising at least one compound selected from the compound of the formula A, preferably the mixture of compounds of the formulae (A.a), (A.b) and (A.c), as aroma chemical.

In preferred embodiment, the present invention relates to the use of a compound of the formula A, preferably the mixture of compounds of the formulae (A.a), (A.b) and (A.c), as aroma chemical.

In yet another embodiment, the present invention relates to the use of a compound of the formula A or of a composition comprising at least two compounds selected from the compound of formula A, more preferably the mixture of compounds of the formulae (A.a), (A.b) and (A.c), as aroma chemical.

In yet another embodiment, the present invention relates to the use as aroma chemical, wherein i) at least one compound selected from the compound of formula A, preferably from the compounds of the formulae (A.a1), (A.b1) and (A.c1), is used for preparing a fragrance and/or aroma having a note of muguet and/or rose,

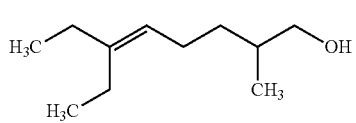
(A.a1)

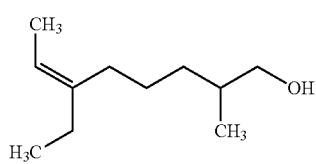
(A.b1)

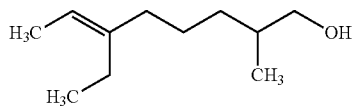
(A.c1)

and/or ii) at least one compound selected from the compound of formula A, preferably from the compounds of the formulae (A.a2), (A.b2) and (A.c2), is used for preparing a fragrance and/or aroma having a note of rose and/or muguet,

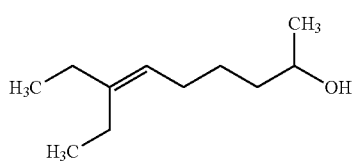
(A.a2)

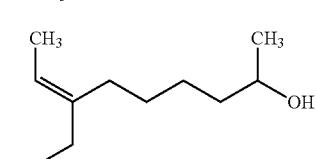
(A.b2)

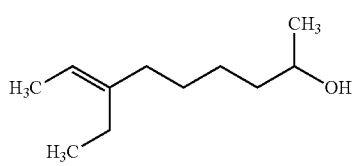
(A.c2)

and/or iii) at least one compound selected from the compound of formula A, preferably from the compounds of the formulae (A.a3), (A.b3) and (A.c3), is used for preparing a fragrance and/or aroma having a note of woody and/or dusty

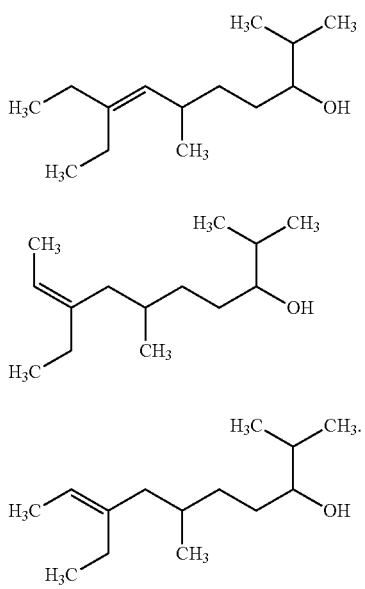

(A.a3)

(A.b3)

(A.c3)

In a preferred embodiment, the present invention relates to the use as aroma chemical, wherein i) the compound of the formula A, preferably mixture of compounds of the formulae (A.a1), (A.b1) and (A.c1), is used for preparing a fragrance and/or aroma having a note of muguet and/or rose,

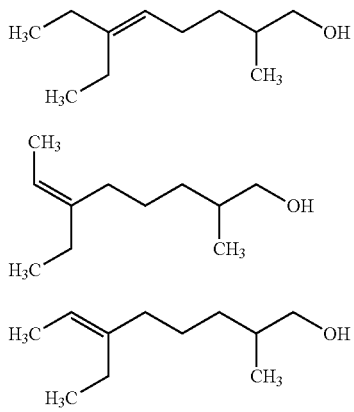

(A.a1)

(A.b1)

(A.c1)

and/or ii) the compound of the formula A, preferably mixture of compounds of the formulae (A.a2), (A.b2) and (A.c2), is used for preparing a fragrance and/or aroma having a note of rose and/or muguet,

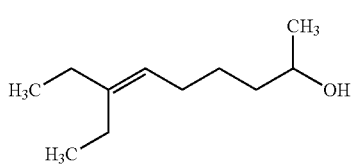

(A.a2)

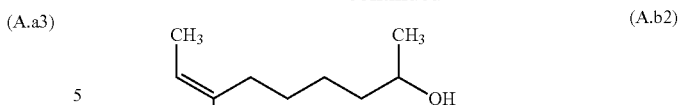

(A.b2)

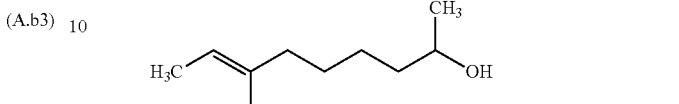

(A.c2)

and/or iii) the compound of the formula A, preferably mixture of compounds of the formulae (A.a3), (A.b3) and (A.c3), is used for preparing a fragrance and/or aroma having a note of woody and/or dusty

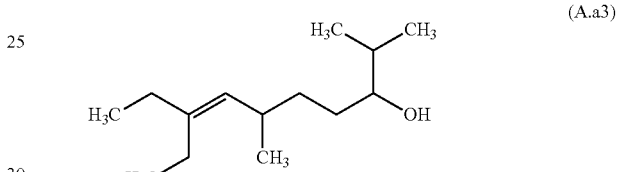

(A.a3)

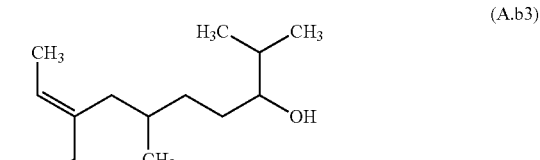

(A.b3)

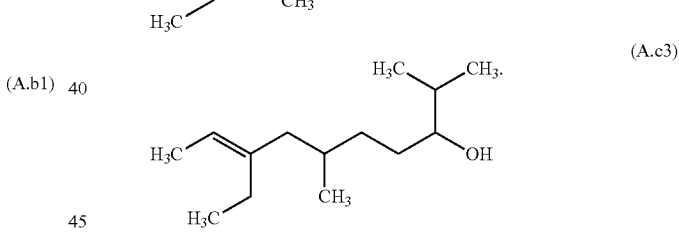

(A.c3)

In yet another preferred embodiment, the present invention relates to the use of a compound, selected from compound of the formulae (A.a), (A.b) and (A.c) or of a composition of at least two compounds selected from compounds of the formulae (A.a), (A.b) and (A.c), as aroma chemical.

In a preferred embodiment, the use of compound of formula A, as aroma chemical in compositions selected from perfumes, detergents and cleaning compositions, cosmetic agents, body care agents, hygiene articles, products for oral and dental hygiene, scent dispensers, fragrances and pharmaceutical agents. In particular, the use of mixture of (A.a), (A.b) and (A.c) in compositions selected from perfumes, detergents and cleaning compositions, cosmetic agents, body care agents, hygiene articles, products for oral and dental hygiene, scent dispensers, fragrances and pharmaceutical agents.

In a preferred embodiment, the present invention relates to an aroma substance and/or fragrance composition comprising i) at least a compound of formula (A) or a composition comprising at least one compound selected from the compound of formula A, preferably the mixture of compounds of the formulae (A.a), (A.b) and (A.c), ii) optionally at least one further aroma chemical different from the component i), and iii) optionally at least one diluent, with the proviso that the composition comprises at least one component ii) or iii).

In one embodiment, the present invention relates to a perfumed or fragranced product comprising at least a compound of formula (A) or a composition comprising at least one compound selected from the compound of formula A, preferably the mixture of compounds of the formulae (A.a), (A.b) and (A.c).

In yet another preferred embodiment, the present invention relates to a method for scenting a product, particularly for imparting and/or enhancing an odor or flavor, in which at least one compound of formula (A) is used and/or in which a composition comprising at least one compound selected from the compound of formula A, preferably the mixture of compounds of the formulae (A.a), (A.b) and (A.c) is used.

Compounds can be characterized e.g. by Nuclear magnetic resonance spectroscopy (NMR), and/or by Gas Chromatography (GC).

SYNTHESIS EXAMPLES

Example 1

Preparation of 6-ethyl-3-methyl-oct-6-en-1-ol

Step-1: 5-methyloxepan-2-one

To the solution of 4-methyl cyclohexanone (50 g, 0.45 mol) in 300 mL dichloromethane (DCM), was added a solution of meta-chloro-perbenzoic acid (mCPBA, ~77%, 130 g, 0.58 mol) in 1 L DCM at 20° C. in 1 h. Stirring was continued at RT for 2 h and the reaction was monitored by GC. After 2 h, GC showed complete conversion of the starting material. The precipitated solid was filtered off and the filtrate was washed with thiosulfate solution followed by bicarbonate solution. The organic phase was dried and the solvent evaporated to obtain 53 g of product (lactone) having GC purity of 98%. Yield 90%.

Step-2: 6-ethyl-3-methyl-octane-1,6-diol

To the cooled solution of ethyl magnesium bromide (500 mL, 1.75 mol) at 0-5° C. in a 3-necked flask was added a solution of 45 g (0.35 mol) of the lactone from the previous step in 50 mL dry THF under N2 atmosphere. After 30 min, the addition was complete and the reaction mixture was allowed to come to RT and was stirred for 2 h. TLC confirmed the completion of the reaction. Then, the reaction was quenched with 800 mL saturated ammonium chloride solution and extracted with ethyl acetate (3×500 mL). The combined organic layer was washed with brine, dried over sodium sulfate and the solvent was evaporated to obtain 58 g crude product which was the tertiary-alcohol having GC purity of 99%. Yield 87%.

Step-3: 6-ethyl-3-methyl-oct-6-en-1-ol

A solution of the tertiary alcohol from the previous step (75 g, 0.40 mol) and para-toluene sulfonic acid (pTSA, 17 g, 0.089 mol) in 500 mL ethylene dichloride was stirred at 60° C. The reaction was monitored by TLC which showed complete disappearance of the starting material after 7 h. The reaction was quenched with bicarbonate solution and the phases separated. The organic layer was dried and the solvent was evaporated to get 65 g of the product having GC purity of 75%. Yield 72%.

Example 2

Preparation of 6-ethyl-2-methyl-oct-6-en-1-ol

Step-1: 6-methyloxepan-2-one

Added the solution of 3-methyl-cyclohexanone (20 g, 0.18 mol) in 200 mL DCM to the stirred suspension of mCPBA (~77%, 48.2 g, 0.21 mol) and NaHCO$_3$ (18 g, 0.21 mol) in 200 mL DCM. Stirred at RT for 6 h. Then, the reaction was stopped by addition of 30 mL saturated aq. KI solution followed by bisulfite solution. Separated the layers, washed the organic layer with water and dried. The solvent was evaporated to get a thick colorless liquid (21.5 g) having GC purity of about 90%. Yield 84%.

Step-2: 6-ethyl-2-methyl-octane-1,6-diol

A solution of the lactone from the previous step (4.5 g, 0.035 mol) in 30 mL THF was added dropwise to the solution of 1 M ethyl magnesium bromide (175 mL, 0.175 mol) in THF at 5-10° C. under N$_2$ atmosphere. After complete addition, the reaction mixture was brought to RT and stirred for 3 h. Then, the reaction was quenched with cold sat. NH$_4$Cl solution (100 mL) and extracted with ethyl acetate (2×50 mL). The combined organic layer was dried and the solvent was evaporated to get 6 g of the crude 6-ethyl-2-methyl-octane-1,6-diol having GC purity 90%. Yield 82%.

Step-3: 6-ethyl-2-methyl-oct-6-en-1-ol

To the solution of the tertiary alcohol from the previous step (6 g, 0.032 mol) in 50 mL DCM was added methane sulfonic acid in 10 min. The reaction mixture was stirred for 3 h and then quenched with bicarbonate solution. The phases were separated and the organic layer was washed with water and dried. The solvent was evaporated to get 5 g of crude dehydrated product (crude yield 92%). This was further purified by column chromatography to get 2 g of product having a purity of 98%.

Example 3

Preparation of 7-ethylnon-7-en-2-ol

Step-1: 7-methyloxepan-2-one

To a solution of 2-methyl-cyclohexanone (5 g, 0.045 mol) in 50 mL DCM was added a solution of mCPBA (~77%, 16 g, 0.072 mol) in 100 mL DCM at 20° C. over a period of 30 min. The reaction mixture was stirred at RT for 5 h. The precipitate was filtered off and the filtrate was washed with thiosulfate solution followed by bicarbonate solution. The organic layer was dried and the solvent evaporated to get 5.1 g crude lactone having GC purity >98%. Yield 87%.

Step-2: 7-ethylnonane-2,7-diol

The solution of the lactone from the previous step (3 g, 0.023 mol) in 20 mL THF was added dropwise to the solution of ethyl magnesium bromide (1 M in THF, 120 mL, 0.12 mol) at 10-20° C. under N₂ atmosphere. After complete addition, the reaction mixture was brought to RT and stirred for 4 h. Then, the reaction was quenched with 2 N HCl (50 mL) and extracted with MTBE (2×50 mL). The combined organic layer was dried and the solvent was evaporated to get 4 g crude alcohol having GC purity >90%. Yield 83%.

Step-3: 7-ethylnon-7-en-2-ol

To the solution of the alcohol from the previous step (4 g, 0.021 mol) in 70 mL Dichloroethane was added pTSA (0.6 g, 0.00324 mol). The reaction mixture was heated to 60° C. and stirred at this temperature for 3 h, before it was quenched with bicarbonate solution. The layers were separated and the organic layer was washed with water and dried. The solvent was evaporated to get 3.4 g crude dehydrated product (crude yield 95%). This was further purified by column chromatography to get 1.2 g of product having a purity of 98%.

Example 4

Preparation of 8-ethyl-2,6-dimethyl-dec-8-en-3-ol

Step-1: 7-isopropyl-4-methyl-oxepan-2-one

To a solution of menthone (10 g, 0.065 mol) in 60 mL DCM was added a solution of mCPBA (~77%, 26 g, 0.116 mol) in 200 mL DCM at 20° C. over a period of 30 min. The reaction mixture was stirred at RT for 18 h. Then, the reaction mixture was washed with thiosulfate solution followed by bicarbonate solution. The organic layer was dried and the solvent was evaporated to get 11 g of crude lactone having GC purity of 97%. Yield 96%.

Step-2: 8-ethyl-2,6-dimethyl-decane-3,8-diol

To a solution of ethyl magnesium bromide (1 M in THF, 88 mL, 0.088 mol) was added the lactone from the previous step (3 g, 0.018 mol) in 25 mL THF dropwise at 5-10° C. under N₂ atmosphere. After complete addition, the reaction mixture was brought to RT and stirred for 1.5 h. Then, the reaction was quenched with sat. NH₄Cl solution and extracted with ethyl acetate (2×50 mL). The combined organic layer was dried and the solvent was evaporated to get 4 g crude tertiary alcohol having GC purity of 88% (crude yield 85%). It was purified by column chromatography to get 2 g of product of GC purity 98%.

Step-3: 8-ethyl-2,6-dimethyl-dec-8-en-3-ol

To the solution of the alcohol from the previous step (6 g, 0.026 mol) in 20 mL DCM cooled to 10-20° C. was added 0.5 mL methane sulfonic acid and the reaction mixture was stirred at RT for 3 h. Then, the reaction was quenched with bicarbonate solution and the layers were separated. The organic layer washed with water and dried and the solvent was evaporated to get 5 g of crude dehydrated product. This was purified by column chromatography and obtained as two fractions: Fraction-1:2 g, GC=95% and fraction-2: 2 g, GC=90%. Yield 67%.

The invention claimed is:

1. A method for preparing a compound of formula (I)

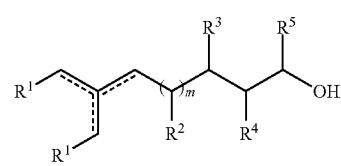

formula (I)

wherein
═══ is a single or a double bond,
wherein formula (I) comprises
the compound of the formula (Ia)

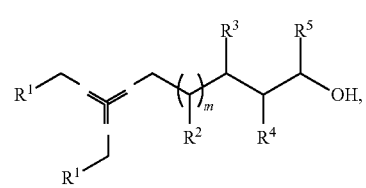

formula (Ia)

the compound of the formula (Ib)

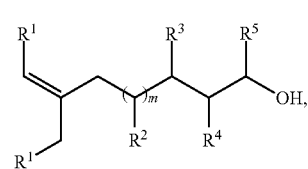

formula (Ib)

and
the compound of the formula (Ic)

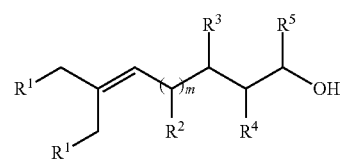

formula (Ic)

and stereoisomers thereof;
whereby m is 0; $R^1$, $R^3$, $R^4$ and $R^5$, identical or different, are selected from the group consisting of H, $C_1$-$C_4$-alkyl and $C_3$-$C_4$-cycloalkyl;
whereby m is 1, 2 or 3 and $R^1$, $R^2$, $R^3$, $R^4$ and $R^5$, identical or different, are selected from the group consisting of H, $C_1$-$C_4$-alkyl and $C_3$-$C_4$-cycloalkyl;
comprising at least the steps of:
a) providing a compound of formula (IIa),

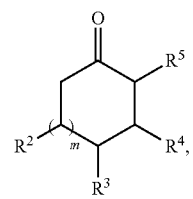

formula (IIa)

whereby m is 0; $R^3$, $R^4$ and $R^5$, identical or different, are selected from the group consisting of H, $C_1$-$C_4$-alkyl and $C_3$-$C_4$-cycloalkyl;

whereby m is 1, 2 or 3; $R^2$, $R^3$, $R^4$ and $R^5$, identical or different, are selected from the group consisting of H, $C_1$-$C_4$-alkyl and $C_3$-$C_4$-cycloalkyl;

b) subjecting the compound of the formula (IIa) to a compound selected from peroxyacids and peroxides to obtain a compound of formula (IIb),

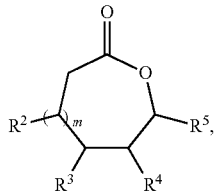

Formula (IIb)

c) reacting the compound of the formula (IIb) with a compound of formula (IIc),

  formula (IIc), wherein $R^1$ is selected from the group consisting of H, $C_1$-$C_4$-alkyl and $C_3$-$C_4$-cycloalkyl; X is Br, Cl or I, to obtain a compound of formula (IId),

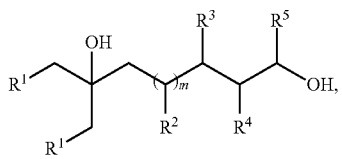

formula (IId)

whereby m is 0; $R^1$, $R^3$, $R^4$ and $R^5$, identical or different, are selected from the group consisting of H, $C_1$-$C_4$-alkyl and $C_3$-$C_4$-cycloalkyl;

whereby m is 1, 2 or 3 and $R^1$, $R^2$, $R^3$, $R^4$ and $R^5$, identical or different, are selected from the group consisting of H, $C_1$-$C_4$-alkyl and C3-C4-cycloalkyl;

d) subjecting the compound of formula (IId) to a dehydration reaction to obtain the compound of the formula (I).

2. The method of claim 1 for preparing compound of formula (I')

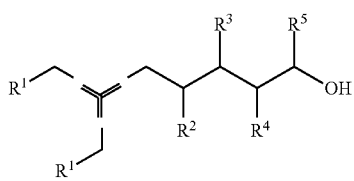

formula (I')

wherein

⎓⎓⎓ is a single or a double bond, wherein formula (I') comprises the compound of the formula (Ia')

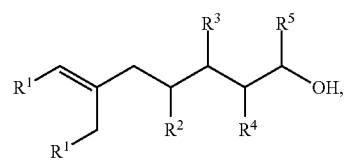

formula (Ia')

the compound of the formula (Ib')

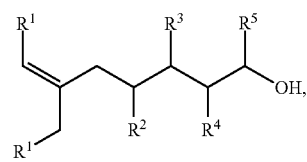

formula (Ib')

and the compound of the formula (Ic')

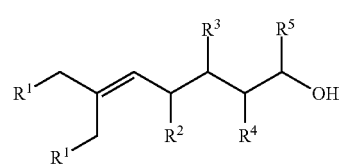

formula (Ic')

and stereoisomers thereof;

wherein $R^1$, $R^2$, $R^3$, $R^4$ and $R^5$, identical or different, are selected from the group consisting of H, $C_1$-$C_4$-alkyl and $C_3$-$C_4$-cycloalkyl;

comprising at least the steps of:

a) providing a compound of formula (IIa'),

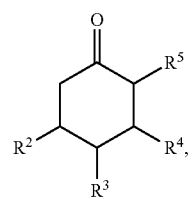

formula (IIa')

wherein $R^2$, $R^3$, $R^4$ and $R^5$, identical or different, are selected from the group consisting of H, $C_1$-$C_4$-alkyl and $C_3$-$C_4$-cycloalkyl;

b) subjecting the compound of the formula (IIa') to a compound selected from peroxyacids and peroxides to obtain a compound of formula (IIb'), formula (IIb')

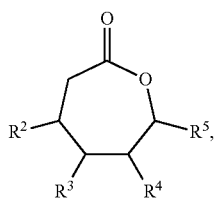

c) reacting the compound of the formula (IIb') with a compound of formula (IIc'),

 formula (IIc'), wherein $R^1$ is selected from the group consisting of H, $C_1$-$C_4$-alkyl and $C_3$-$C_4$-cycloalkyl; X is Br, Cl or I, to obtain a compound of formula (IId'), formula (IId')

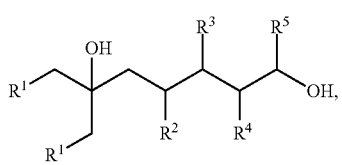

wherein $R^1$, $R^2$, $R^3$, $R^4$ and $R^5$, identical or different, are selected from the group consisting of H, $C_1$-$C_4$-alkyl and $C_3$-$C_4$-cycloalkyl;

d) subjecting the compound of formula (IId') to a dehydration reaction to obtain the compound of the formula (I').

3. The process according to the claim 1, wherein steps (b), (c) and (d) and/or steps (b) and (c) and/or steps (c) and (d) are carried out in a single pot.

4. The process according to the claim 1, wherein the peroxyacid in step b) is selected from the group consisting of peroxymonosulfuric acid, peroxyphosphoric acid, peroxyacetic acid, peroxyformic acid, peroxytrifluoroacetic acid, potassium peroxymonosulfate, sodium perborate, peroxynitric acid and peroxybenzoic acid.

5. The process according to the claim 4, wherein the peroxybenzoic acid is metachloroperoxybenzoic acid.

6. The process according to the claim 1, wherein the peroxide in step b) is selected from the group consisting of hydrogen peroxide.

7. The process according to claim 1, wherein step d) is carried out in the presence of an acid.

8. The process according to claim 7, wherein the acid is selected from the group consisting of methanesulfonic acid, phosphoric acid, p-toluenesulfonic acid, formic acid, sulfuric acid, hydrochloric acid and acetic acid.

9. A compound of the formula (A.a2), (A.b2), (A.c2), (A.a3), (A.b3) or (A.c3), (A.a2)

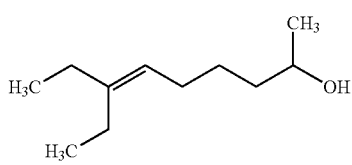

(A.b2)

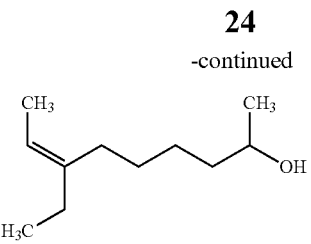

(A.c2)

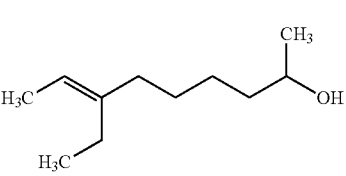

(A.a3)

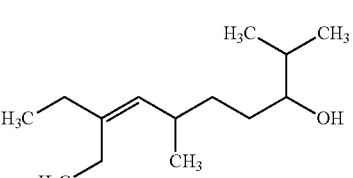

(A.b3)

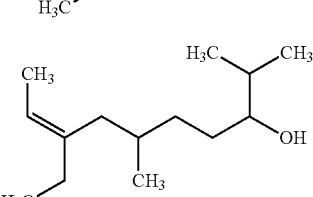

(A.c3)

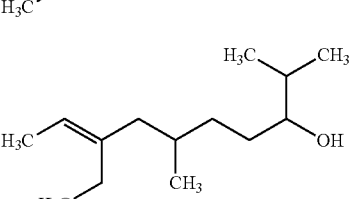

and stereoisomers thereof.

10. A composition comprising at least one compound selected from the mixture of compounds of the formulae (A.a2), (A.b2), (A.c2), (A.a3), (A.b3) or (A.c3) according to claim 9.

11. An aroma the compound of the formula A formula A

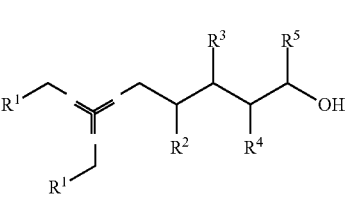

wherein

⎓ is a single or a double bond, wherein formula A comprises
the compound of the formula (A.a), formula (A.a)

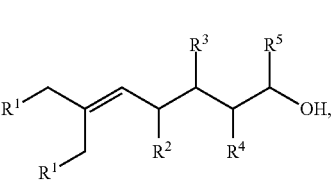

the compound of the formula (A.b),

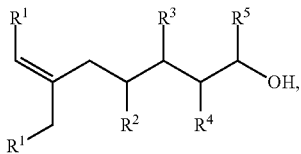
formula (A.b)

and
the compound of the formula (A.c)

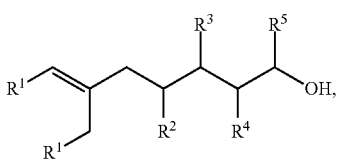
formula (A.c)

wherein R$^1$, R$^2$ and R$^5$, identical or different, are selected from the group consisting of H, C$_1$-C$_4$-alkyl and C$_3$-C$_4$-cycloalkyl;

R$^4$ is selected from the group consisting of H, C$_2$-C$_4$-alkyl and C$_3$-C$_4$-cycloalkyl;

R$^3$ is H;

and stereoisomers thereof, with a proviso that when R$^1$ is H or methyl then at least one of the R$^2$, R$^4$ and R$^5$ is not H.

12. The use aromatic chemical according to claim 11, wherein
i) the at least one compound selected from the compound of the formulae (A.a1), (A.b1) and (A.c1), is used for preparing a fragrance and/or aroma having a note of muguet and/or rose,

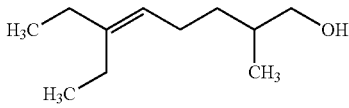
(A.a1)

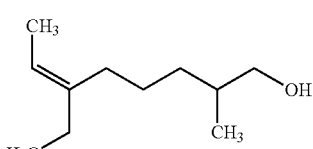
(A.b1)

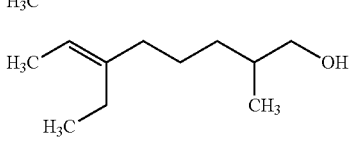
(A.c1)

and/or
ii) the at least one compound selected from the compound of the formulae (A.a2), (A.b2) and (A.c2), is used for preparing a fragrance and/or aroma having a note of rose and/or muguet,

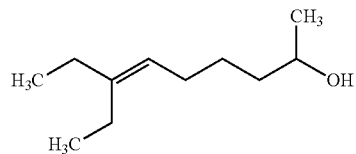
(A.a2)

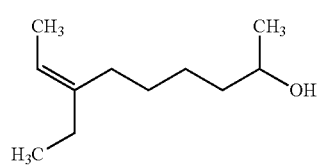
(A.b2)

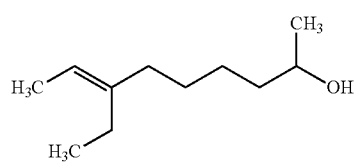
(A.c2)

and/or
iii) the at least one compound selected from the compound of the formulae (A.a3), (A.b3) and (A.c3), is used for preparing a fragrance and/or aroma having a note of woody and/or dusty

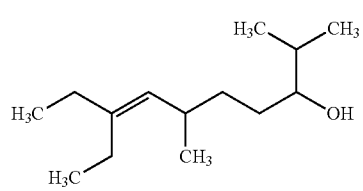
(A.a3)

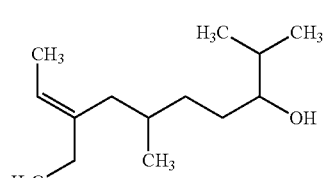
(A.b3)

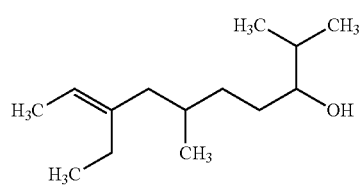
(A.c3)

13. The aromatic chemical according to claim 12, wherein
i) the compound of the formulae (A.a1), (A.b1) and (A.c1), is used for preparing a fragrance and/or aroma having a note of muguet and/or rose,

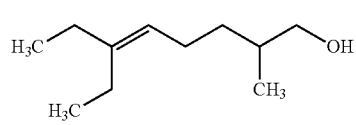
(A.a1)

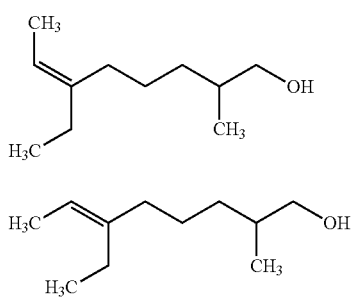

(A.b1)

(A.c1)

and/or ii) the compound of the formulae (A.a2), (A.b2) and (A.c2), is used for preparing a fragrance and/or aroma having a note of rose and/or muguet,

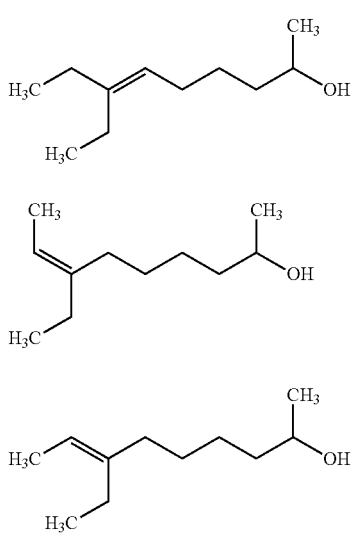

(A.a2)

(A.b2)

(A.c2)

and/or iii) the compound of the formulae (A.a3), (A.b3) and (A.c3), is used for preparing a fragrance and/or aroma having a note of woody and/or dusty

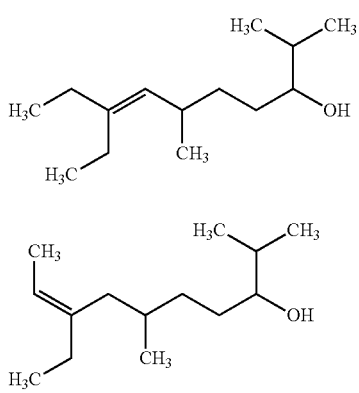

(A.a3)

(A.b3)

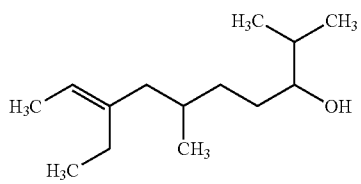

(A.c3)

14. A composition comprising the aromatic chemical according to claim 11 wherein the composition is selected from perfumes, detergents and cleaning compositions, cosmetic agents, body care agents, hygiene articles, products for oral and dental hygiene, scent dispensers, fragrances and pharmaceutical agents.

15. An aroma substance and/or fragrance composition comprising
   i) at least a compound of the formula (A) according to claim 9,
   ii) optionally at least one further aroma chemical different from the component i), and
   iii) optionally at least one diluent,
   with the proviso that the composition comprises at least one component ii) or iii).

16. A perfumed or fragranced product comprising at least a compound of the formula (A) according to claim 9.

17. A method for scenting a product in which at least one compound of the formula (A) according to claim 9 is used.

18. A process for preparing a fragrance and/or aroma having a note of muguet and/or rose or a note of woody and/or dusty which comprises utilizing the aromatic chemical according to claim 11, wherein
   i) the at least one compound selected from the compound of the formulae (A.a1), (A.b1) and (A.c1), is used for preparing a fragrance and/or aroma having a note of muguet and/or rose,

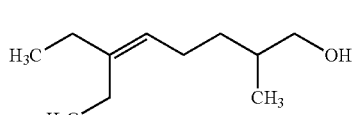

(A.a1)

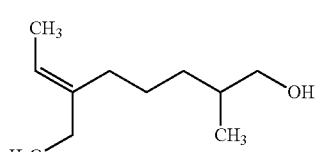

(A.b1)

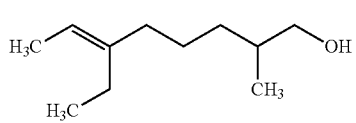

(A.c1)

and/or ii) the at least one compound selected from the compound of the formulae (A.a2), (A.b2) and (A.c2), is used for preparing a fragrance and/or aroma having a note of rose and/or muguet,

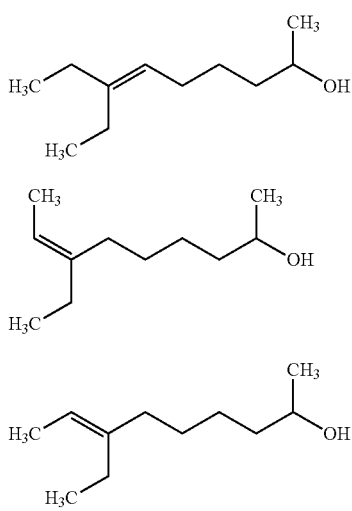

(A.a2)

(A.b2)

(A.c2)

and/or
iii) the at least one compound selected from the compound of the formulae (A.a3), (A.b3) and (A.c3), is used for preparing a fragrance and/or aroma having a note of woody and/or dusty

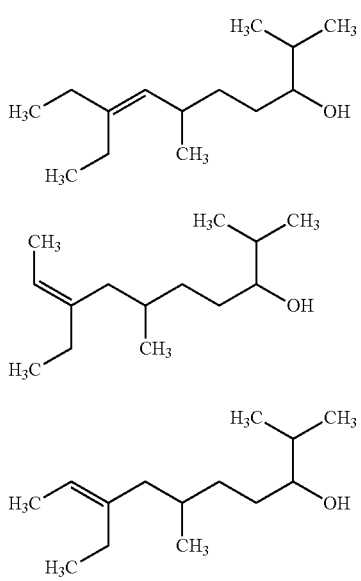

(A.a3)

(A.b3)

(A.c3)

19. A process for preparing a fragrance and/or aroma having a note of muguet and/or rose or a note of woody and/or dusty which comprises utilizing the aromatic chemical according to claim 11, wherein
i) the compound of the formulae (A.a1), (A.b1) and (A.c1), is used for preparing a fragrance and/or aroma having a note of muguet and/or rose,

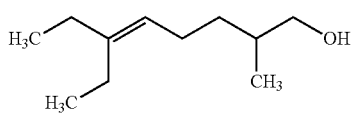

(A.a1)

-continued

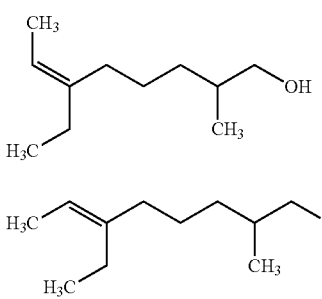

(A.b1)

(A.c1)

ii) the compound of the formulae (A.a2), (A.b2) and (A.c2), is used for preparing a fragrance and/or aroma having a note of rose and/or muguet,

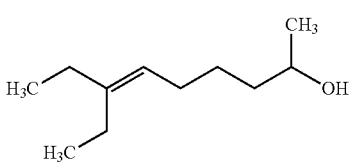

(A.a2)

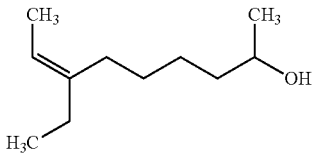

(A.b2)

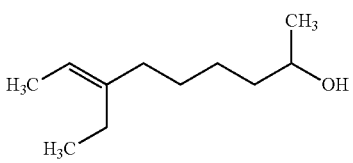

(A.c2)

and/or
iii) the compound of the formulae (A.a3), (A.b3) and (A.c3), is used for preparing a fragrance and/or aroma having a note of woody and/or dusty

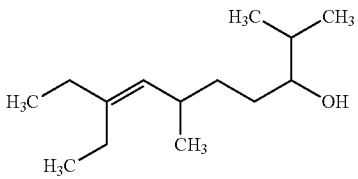

(A.a3)

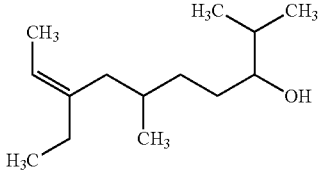

(A.b3)

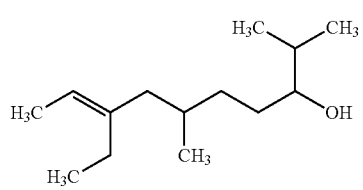
(A.c3)
* * * * *